(12) United States Patent
Ye et al.

(10) Patent No.: US 8,152,733 B2
(45) Date of Patent: Apr. 10, 2012

(54) METHOD FOR IMPROVING RECOGNITION RATE OF RESPIRATORY WAVE

(75) Inventors: Jilun Ye, Nanshan (CN); Yulin Yang, Nanshan (CN); Yun Deng, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1477 days.

(21) Appl. No.: 11/605,746

(22) Filed: Nov. 29, 2006

(65) Prior Publication Data

US 2007/0135726 A1 Jun. 14, 2007

(30) Foreign Application Priority Data

Dec. 8, 2005 (CN) .......................... 2005 1 0102392

(51) Int. Cl.
    *A61B 5/08* (2006.01)
(52) U.S. Cl. .................. 600/529; 600/301; 600/484
(58) Field of Classification Search .................. 600/300, 600/329–343
See application file for complete search history.

(56) References Cited

U.S. PATENT DOCUMENTS

| | | | | |
|---|---|---|---|---|
| 5,092,343 A * | 3/1992 | Spitzer et al. | ............ | 600/515 |
| 5,143,078 A * | 9/1992 | Mather et al. | ............ | 600/529 |
| 5,150,323 A * | 9/1992 | Castelaz | ............ | 708/801 |
| 5,682,898 A | 11/1997 | Aung et al. | | |
| 5,751,911 A | 5/1998 | Goldman | | |
| 6,816,741 B2 * | 11/2004 | Diab | ............ | 600/324 |
| 7,758,503 B2 * | 7/2010 | Lynn et al. | ............ | 600/300 |
| 2002/0109550 A1 * | 8/2002 | Dolman et al. | ............ | 330/284 |
| 2004/0260186 A1 | 12/2004 | Dekker | | |
| 2008/0039725 A1 * | 2/2008 | Man et al. | ............ | 600/454 |
| 2009/0182211 A1 * | 7/2009 | Diab et al. | ............ | 600/323 |

FOREIGN PATENT DOCUMENTS

CN 1559344 A 1/2005

OTHER PUBLICATIONS

Adaptive Modeling of Sound Transmission in the Respiratory System; K. Ciftci, M. Yeginer, I. Sen, U. Cini, and Y. P. Kahya; Proceedings of the 26th Annual International Conference of the IEEE EMBS, San Francisco, CA, USA, Sep. 1-5, 2004; 3824-3827.* Real-Time Monitoring of Respiration Rhythm and Pulse Rate During Sleep; Xin Zhu, Wenxi Chen, Tetsu Nemoto, Yumi Kanemitsu, Kei-ichiro Kitamura, Ken-ichi Yamakoshi, and Daming Wei; IEEE Transactions on Biomedical Engineering, vol. 53, No. 12, Dec. 2006, 2553-2563.*
Li, Gran et al., "Application of Impedance Pneumograph for Monitoring Respiratory Function," Research Institute of Biomedical Engineering, Xi'an Jiaotong University, Xi'an 710049, pp. 87-93.
Baohua, Liu, "The Design of a New Respiratory Detecting System Using Impedance Method," Yon Shan University, Qux Huangdao 066004, Jun. 5, 2003, pp. 527-530.
Li, Gran et al., "Application of Impedance Pneumograph for Monitoring Respiratory Function," Research Institute of Biomedical Engineering, Xi'an Jiaotong University, Xi'an 710049, Feb. 25, 1995, pp. 87-93.

* cited by examiner

*Primary Examiner* — Patricia Mallari
*Assistant Examiner* — Karen Toth
(74) *Attorney, Agent, or Firm* — Kory D. Christensen; Stoel Rives LLP

(57) ABSTRACT

The present invention discloses a method for improving recognition rate of respiratory wave, which is used for a data processing module of a respiratory rate measuring or monitoring device, specifically, said method comprises the steps of: receiving, via a data processing module, respiratory wave data which come from a measuring circuit and have been analog-to-digital converted; according to the feature that each crest or trough signal in the respiratory wave data has rising stairs and falling stairs, sequentially searching for and finding out, based on a predetermined number of stairs, the data corresponding to each crest and trough via said data processing module; and determining each crest and trough in a corresponding respiratory wave. According to the present invention, interferences may be effectively eliminated and recognition rate of respiratory waveform may be effectively improved, so that the computation of respiratory rate will be more accurate and stable, and the measuring or monitoring device will have a higher clinical practicability.

14 Claims, 5 Drawing Sheets

METHOD FOR IMPROVING RECOGNITION RATE OF RESPIRATORY WAVE

FIELD OF THE INVENTION

The present invention relates to a measuring or monitoring device for medical diagnosis, and in particular, to a method for processing data collected from respiratory wave in a respiratory rate measuring or monitoring device.

BACKGROUND OF THE INVENTION

In the prior art, respiratory wave signals are obtained through a respiration measuring device by using an impedance-based measuring method. In this method, a high frequency carrier wave signal is applied to the human thoracic cavity by means of an AgCl electrode stuck to a certain position on the body surface of the human during the monitoring of body surface electrocardio-signals. The human thoracic cavity with a constant volume will have a constant basic impedance with respect to the high frequency carrier wave, so when respirations result in the change in the volume of the thoracic cavity, the impedance of thoracic cavity will change slightly. As a result, the respiratory change may be reflected by this slight change in the impedance of thoracic cavity and may be further modulated on the high frequency carrier wave signal. The high frequency carrier wave signal modulated by human respiration may be fed to a respiration amplifying circuit via an electrocardio-cable, and then carrier wave amplification, carrier wave detection and demodulation and respiratory wave amplification will be performed. Finally, a volt-level respiration signal will be obtained. After A/D (analog-to-digital) conversion, a digital respiratory wave signal will be provided, which can be used for respiratory wave feature recognition and respiratory rate computation.

Usually, the respiration rhythm of human is relatively stable. The normal respiratory rate of an adult is 10-30 BPM (Beats per Minute), and the normal respiratory rate of an infant is 30-70 BPM. Therefore, in consideration of abnormal circumstances, the detection range of a respiration detection circuit is usually required to be 8-120 BPM, and sometimes it is required to be up to 150 BPM. The frequency of the respiratory wave corresponding to such range of respiratory rate is about 0.125-2.5 Hz. Due to the individual difference between human bodies, the basic impedance of thoracic cavity of a human is usually about 200-5000 ohm, and the variation of the impedance of thoracic cavity caused by respirations is about 0.3-3 ohm. As a result, the original respiration signal generated by the impedance variation is in the magnitude of tens of microvolts (such as 0.05-0.5 mV).

The process for measuring the respiration signal by means of impedance is prone to undergo interferences, which mainly come from limb movements and cardiac blood-ejection activities causing the variation of the impedance of thoracic cavity of a human. In the respiration measuring process, especially for infants, limb movements cannot be avoided. The variations of thoracic and abdominal impedances caused by limb movements sometimes are sufficient to exceed the slight variation of impedance caused by human respiration. In this case, respiration signals cannot be detected and recognized. Similarly, depending on the differences between individuals, the variation of the impedance of thoracic cavity caused by cardiac blood-ejection activities may also affect respiration signals. It has been found that for some individuals under test, heartbeat activities cause so great interference on respiration signals that Cardiovascular Artifact (CVA) will appear. As a result of such interference, the measuring device wrongly recognizes heartbeat signals as respiration signals, so that the respiratory rate thus computed will be higher than it actually is.

Respiratory rate computation and asphyxia alarm are the two main tasks of respiration measuring. Accurate respiratory rate and accurate asphyxia alarm depend on high recognition rate of respiratory wave. Usually, filtering is performed by lowpass or bandpass filters. Waveform recognition is implemented by a recognizing method based on baseline (i.e., the mean value of the amplitudes during a period of time) threshold or variation threshold. The existence or inexistence of respiratory wave during a certain period of time is determined by comparing the position of the respiratory wave relative to its baseline, and the respiratory rate is computed by an averaging method.

The above method of the prior art is advantageous in that the recognizing process is relatively intuitionistic. However, the shortages of this method are: when there exist limb movement interference and baseline drift caused by it, miss-recognitions of the respiratory wave may appear with this method; wrong asphyxia alarms may be generated when the strength of respiration is unstable; and wrong waveform recognitions may be generated especially when CVA interference exists. In conclusion, this method can't resist various interferences and is insensitive to signal variations, resulting in the inaccuracy and instability of the respiratory rate measurement.

SUMMARY OF THE INVENTION

In view of the deficiencies of the prior art, it is an object of the present invention to provide a method for improving recognition rate of respiratory wave, which is used for respiratory rate measuring or monitoring device, so that the respiratory rate can be accurately computed and the asphyxia alarm can be accurately generated.

In order to solve the above technical problems, the basic concept of the present invention is as follows. Because a respiratory wave is a test signal generated based on the variation of the impedance of thoracic cavity, and the variation is initiated by respiration, the respiratory wave is characterized in that it has periodic crests and troughs. If these crests and troughs can be correctly recognized, then correct waveform recognition and accurate respiratory rate computation can be insured. Therefore, in the present invention, according to the characteristic that the rising or falling of the same crest or trough signal has certain stairs in an established model, crest or trough recognition is performed on the collected data with a predetermined number of stairs. Additionally, the true or false of a recognized crest or trough may be further judged via a self-adaptive threshold method.

A technical solution of the present invention provides a method for improving recognition rate of respiratory wave, which is used for a data processing module of a respiratory rate measuring or monitoring device, said method comprising the steps of:

A. receiving, via a data processing module, respiratory wave data which come from a measuring circuit and have been analog-to-digital converted;

C. determining each crest and trough in a corresponding respiratory wave;

and especially, said method further comprises the step of:

B. according to the feature that each crest or trough signal in the respiratory wave data has rising stairs and falling stairs, sequentially searching for and finding out, based on a predetermined number of stairs, the data corresponding to each crest and trough via said data processing module.

Therefore, in said method, a predetermined number of stairs may be employed to eliminate interference crest and interference trough with small amplitudes.

In the above technical solution, the searching process of said step B comprises the steps of:

a. comparing said respiratory wave data with data received before so as to determine whether the corresponding waveform is rising or falling;
b. recording the positions of the maximum or minimum values of the rising or falling in the searched data, when said rising or falling reaches its predetermined extent;
c. judging whether the overall tendency of the current data in the waveform is falling or rising so as to determine whether to recognize retroactively the recorded extremal position as the previous crest or trough; and
d. taking the next respiratory wave data and returning to step a until the searching process completes.

In the above technical solution, said step C comprises: judging whether the amplitude or frequency variation of the waveform extends beyond a predetermined range according to the data corresponding to each of the currently searched crests and troughs; when it extends beyond the predetermined range, a heartbeat filtering processing is started in step A.

In the above technical solution, said heartbeat filtering is realized via a FIR filter $$y(n) = \frac{1}{L}\sum_{k=0}^{L-1} x(n-k),$$

where x(n) is the measured respiratory wave data, y(n) is the result obtained after the heartbeat filtering of said data, and L is approximately the number of sampling points of the respiration in a heartbeat cycle.

In the above technical solution, said step C further comprises: judging whether the amplitude or cycle variation of waveform is within a predetermined range according to the data corresponding to each of the currently searched crests and troughs; if the variations of the amplitude and cycle of waveform are within the predetermined range (i.e., if a fluctuation of said amplitude is small and said cycle meets predetermined requirements) in a predetermined time period, then an amplification coefficient of the received data will be increased in step A or before step A; and if the variations of the amplitude and cycle of waveform are not within the predetermined range in a predetermined time period (e.g., if the signal is in an amplified state and a cut-off state occurs in a predetermined time period), then said amplification coefficient will be decreased.

In the above technical solution, said step C further comprises the steps of judging true or false of each of said crests and troughs by using a self-adaptive threshold method, comprising:

i. obtaining a series of threshold parameters by sensitivity settings, said threshold parameters including parameters for judging true or false of respiratory crests and troughs;
ii. dividing each of the respiratory crests or troughs recognized in said step B into various types by using said threshold parameters; and
iii. determining and selecting real crests and troughs.

In the above technical solution, the types of said respiratory crests or troughs include real crest, real trough, false crest or false trough.

By means of the above technical solutions, interferences including CVA may be effectively eliminated in an interfered state, so that the recognition rate of respiratory waveform may be improved, the effective respiratory rate may be computed easily, and high accuracy and stability of the computed value may be insured while wrong alarms may be minimized. Meanwhile, crests and troughs can be obtained directly according to the method of the present invention, and a rapid data response speed can be realized even in an interfered state, so that the measuring or monitoring device will have a higher clinical practicability.

DETAILED DESCRIPTION OF THE EMBODIMENTS

Figure 1:
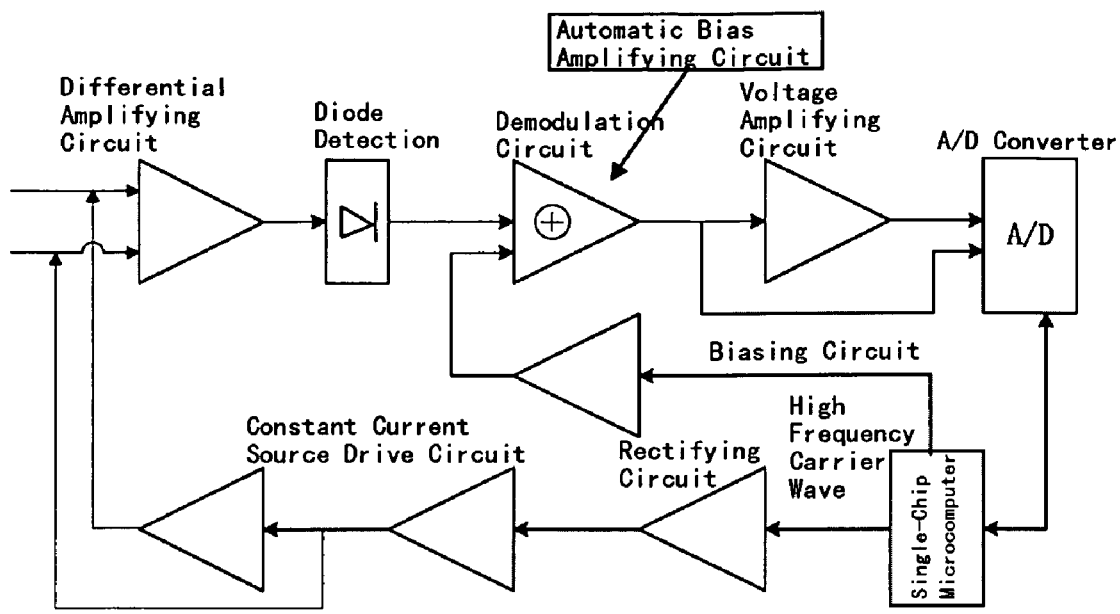
FIG. 1 is a block diagram showing the hardware for measuring respiratory wave signals in the existing measuring or monitoring device.

The present invention will now be further illustrated in conjunction with the preferred embodiments shown in the drawings.

A measuring or monitoring device for measuring respiratory wave signals may be shown in (but not limited to) FIG. 1, which comprises an upper machine and a lower machine. The lower machine comprises a constant current source drive circuit, a backing stage carrier wave signal amplifying circuit, a diode detection circuit, an automatic bias voltage regulating circuit based on digital feedback, an analog-to-digital converting circuit, a single-chip microcomputer system and a rectifying circuit, all of which constitute a modularized respiratory waveform monitoring system. Wherein, the single-chip microcomputer system in cooperation with software is in charge of monitoring the state of the measuring process, collecting the direct current level data obtained after the demodulation of carrier wave, regulating the bias voltage and the feedback, monitoring the effect of bias regulation, collecting respiratory wave signals, processing wrong information and communicating with a control system of the upper machine, etc. The other circuits are mainly in charge of outputting high frequency carrier wave constant current source signals and extracting, demodulating, amplifying and analog-to-digital converting respiratory carrier wave signals, etc. In the lower machine, a constant current source-type carrier wave signal drive source and an amplifying circuit with digital feedback-type bias regulation function are adopted, so that carrier wave signals may have a strong adaptability for different basic impedances, a rapid recovery capability of the circuits after respiratory wave saturation may be reinforced, and the amplifying circuit may have a simple structure. Such a device has been disclosed in the Chinese Patent Application No. 200410015387.4 (Method And Apparatus For Monitoring Human Respiratory Wave Based On The Impedance Variation Principle) of the present applicant, so it will not be described in detail herein.

In view of the poor arithmetic capability of said single-chip microcomputer, an upper machine is provided in this embodiment. The upper machine receives data collected from respiratory wave from a lower machine or stored temporarily in other monitoring devices, and processes the data via a data processing module. According to the method of the present invention, the defect of low recognition rate existing in the prior art is eliminated, so that the computation result of the respiratory rate is compensated and improved, and the measuring or monitoring device has a higher clinical practicability. The method of the invention comprises the steps of:

A. receiving said respiratory wave data via a data processing module;

B. according to the feature that each crest or trough signal in the respiratory wave data has rising stairs and falling stairs, sequentially searching for and finding out, based on a predetermined number of stairs, the data corresponding to each crest and trough via said data processing module; and C. determining each crest and trough in a corresponding respiratory wave.

Figure 3:
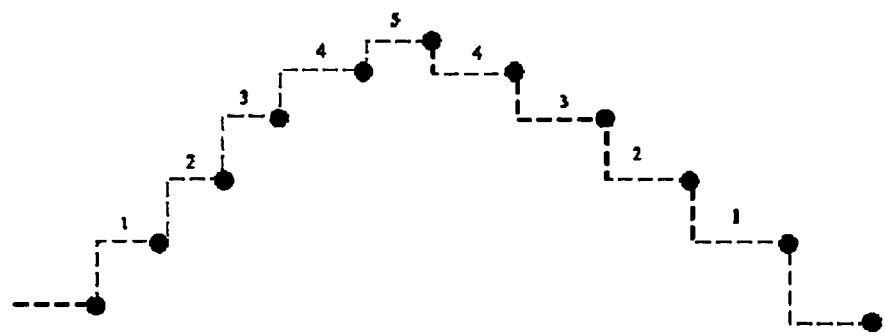
FIG. 3 is a crest model view of the present invention.
Figure 4:
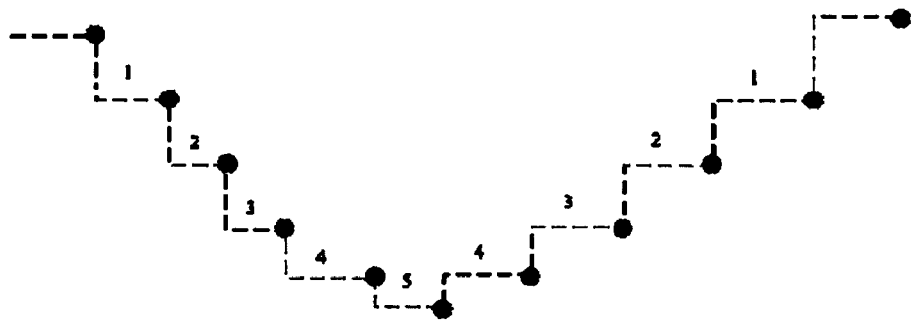
FIG. 4 is a trough model view of the present invention.

Wherein, for the basis of step B, a crest and trough model established according to the present invention shown in FIG. 3 and FIG. 4 may be referred to, in which each horizontal dashed line represents a stair, indicating several (number not limited) neighbouring equal data in the collected data; each perpendicular dashed line represents the amplitude difference between neighbouring two stairs, namely neighbouring two unequal data, and the magnitude of the amplitude difference is not limited; thus, in case of the same rising stairs and falling stairs, the crest or trough represented by this model may have different height and different width. If different rising stairs and falling stairs are taken into consideration, this model may be applicable to any crest or trough. For respiratory wave signals superimposed with interference signals, the data searching process corresponding to said step B may comprise the steps of:

a. comparing said respiratory wave data with data received before so as to determine whether the corresponding waveform is rising or falling; when the current data is larger than the previous data, the waveform is partially rising; otherwise, it is partially falling;

b. recording the positions of the maximum or minimum values of the rising or falling in the searched data, when said rising or falling reaches its predetermined extent;

c. judging whether the overall tendency of the current data in the waveform is falling or rising so as to determine whether to recognize retroactively the recorded extremal position as the previous crest or trough; and d. taking the next respiratory wave data and returning to step a until the searching process completes.

In one embodiment of the invention, several count parameters are provided to judge the overall tendency of rising or falling of said waveform. In order to be intuitionistic, said parameters comprise a rising count, a maximum rising count, a falling count and a maximum falling count. In step B, these parameters may be initialized to 0. In step a, when the current data is larger than the previous data, if said rising count is less than twice of said predetermined number of stairs, then said rising count is increased by 1; if said falling count is larger than 0, then said falling count is decreased by 1; and if said maximum rising count is less than said rising count, then it is set as the value of said rising count. When the current data is less than the previous data, if said falling count is less than twice of said predetermined number of stairs, then said falling count is increased by 1; if said rising count is larger than 0, then said rising count is decreased by 1; and if said maximum falling count is less than said falling count, then it is set as the value of said falling count. As a result, in step c, the judging condition of said overall tendency may be set as: the values of said rising count and falling count are both equal to said predetermined number of stairs (in this case, if the maximum rising count is twice of the predetermined number of stairs, indicating that it is in a falling tendency, then the recorded extremal position may be recognized retroactively as the previous crest and the maximum rising count is set as 0; if the maximum falling count is twice of the predetermined number of stairs, indicating that it is in a rising tendency, then the recorded extremal position may be recognized retroactively as the previous trough and the maximum falling count is set as 0); otherwise, the positions corresponding to said data lie in the original rising or falling tendency of the waveform.

In step b, if the current data is larger than the previous data, i.e., rising, then said predetermined extent will be set as: said rising count and maximum rising count are equal to twice of said predetermined number of stairs, and in this case, said falling count and maximum falling count are 0; if the current data is less than the previous data, i.e., falling, then said predetermined extent will be set as: said falling count and maximum falling count are equal to twice of said predetermined number of stairs, and in this case, said rising count and maximum rising count are 0.

Wherein, the occasion in which the maximum rising count and the maximum falling count are set as 0 according to waveform variation is not defined solely by the above embodiment.

The present embodiment may be realized via an entry function and a data structure, and the data structure can be defined in C Language as follows:

```
typedef struct            //support all information in the crest and
                              trough detection
{
    INT UpCnt ;           //rising count
    INT DownCnt ;         //falling count
    INT UpCntMax ;        //maximum rising count
    INT DownCntMax ;      //maximum falling count
    INT predata ;         //the previous data
    INT amp ;             //amplitude of crest or trough
    INT pos ;             //the current position and the deviation of
                              crest or trough
} FindPeakValleyType,*PFindPeakValleyType;
```

The entry function is defined as follows:

```
INT PeakValleyDetect( INT data,           //the current data
    FindPeakValleyType* pFindPV,    //data state and data structure
    INT &Amplitude,                  //return amplitude
    INT &Position,                   //return position deviation
    INT Criterion )     //predetermined number of stairs
```

The return value of said function may be defined as: 1, which represents a crest; −1, which represents a trough; and 0, which represents neither crest nor trough.

Figure 6:
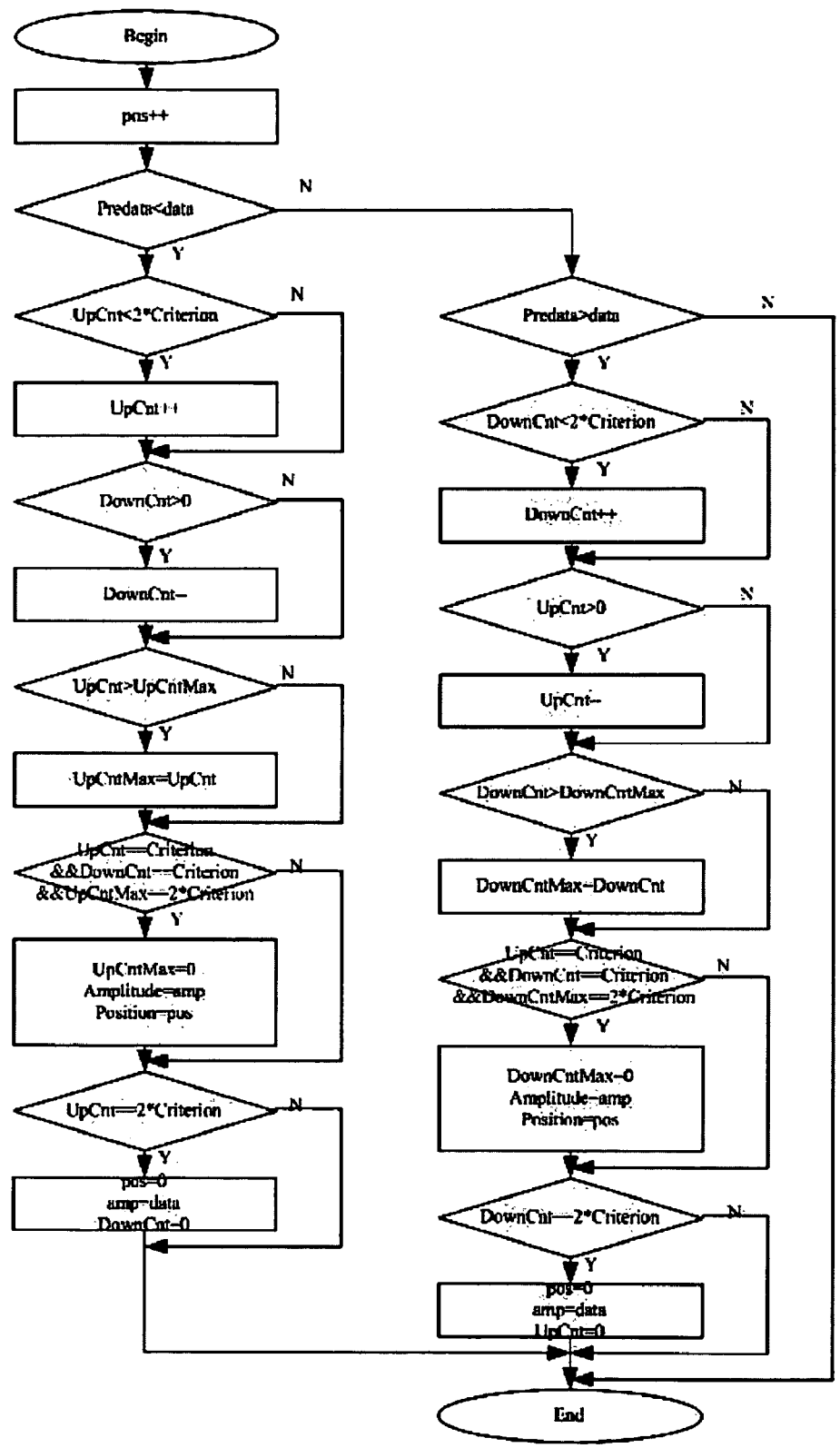
FIG. 6 is a detailed flow chart of crest and trough recognition of the present invention.

Thus, as shown in the flow chart of FIG. 6, the data corresponding to the last UpCnt=2*Criterion, DownCnt=0, UpCntMax=2*Criterion and DownCntMax=0 in a section of data search will be recorded as the maximum value of said rising tendency, and it is set as pos=0; when the search continues to UpCnt=Criterion, DownCnt=Criterion and UpCntMax=2*Criterion, the previous recorded value may be determined as a crest; the pos obtained reflects the positional deviation between the current position and said crest, and it is returned as a parameter Position; while the amplitude of said crest is returned as a parameter Amplitude. The searching process of a trough is in a similar way, so it will not be described in detail herein. The advantages of such a recognition manner are: the crest and trough can be obtained directly, and waves of any waveforms, even square waves having a cut-off state, can be recognized; moreover, the amount of computation is very low.

In the above embodiment, a plurality of count parameters for judging the overall tendency of rising or falling of said waveform may also be provided in other ways, so that the predetermined extent and the judgment standard of the falling tendency or rising tendency of the waveform may be adjusted correspondingly. All of these manners fall within the scope of the present invention, so long as they also employ stairs to simulate crest and trough variation and employ a predetermined number of stairs to eliminate the effect of superimposed interference signals on the judgment of crest and trough.

Figure 5:
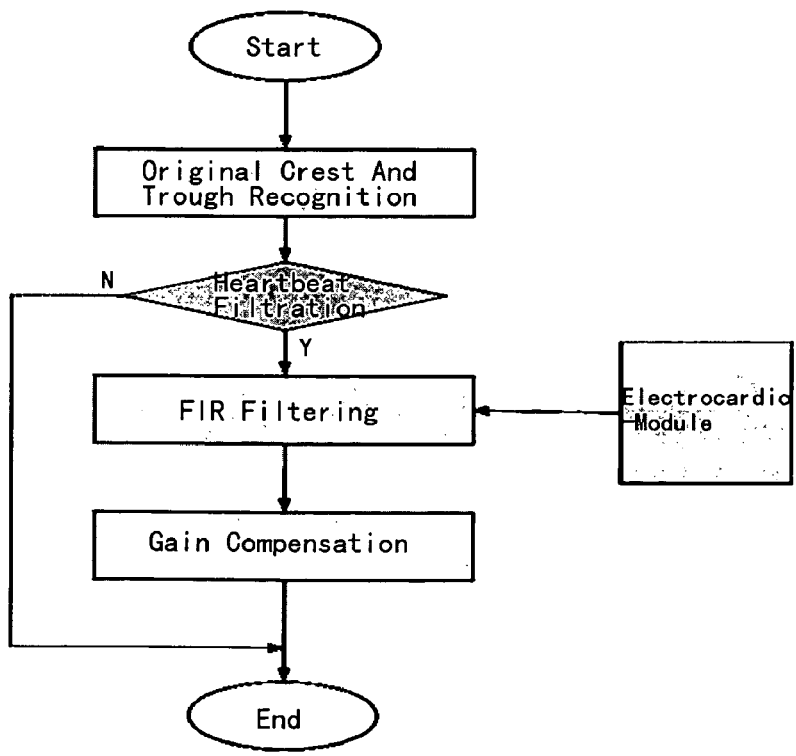
FIG. 5 is a flow chart of the heartbeat filtration processing contained in the method of the present invention.

A great deal of clinical data indicate that heartbeat interference exists in the respiration signal of about 20% individuals. The heartbeat interference ultimately takes the form of a low frequency signal in the range of 0.5 to 4Hz, which is superimposed in the respiration signal. If the heartbeat interference is very strong, then a false crest or false trough will inevitably exist in the recognized crests and troughs; especially when the respiration signal is relatively weak, this interference will be adverse to the gain regulation of the measuring circuit. As shown in FIG. 5, step C of the method according to the present invention further comprises a judgment step of: judging whether the amplitude or frequency variation of the waveform extends beyond a predetermined range according to the data corresponding to each of the currently searched crests and troughs. When it extends beyond the predetermined range, a heartbeat filtering will be started in step A. Said heartbeat filtering may be realized via a FIR (Finite Impulse Response) filter.

The heartbeat speed of an individual is usually larger than the respiratory rate, and the heartbeat interference may be regarded as a periodic signal, the period of which may be different for different individuals or for different timings of the same individual. The following integration function may be employed:

$$y(t) = \frac{1}{T_c} \int_{t-T_c}^{t} x(u)du$$

Where, x(u) is a heartbeat interference signal having the cycle of T; let $T_c \rightarrow T$, then $y(t) \rightarrow C$ (Constant); thus, the heartbeat interference signal will be eliminated from the respiration signal. This integration process can be realized via a FIR filter:

$$y(n) = \frac{1}{L} \sum_{k=0}^{L-1} x(n-k)$$

Where, x(n) is the measured respiratory wave data, and y(n) is the result obtained after the heartbeat filtering of said data; when L is approximately the number of sampling points of the respiration in a heartbeat cycle, the heartbeat interference with varying heartbeat rate may be filtered by the above gradual change process to the heartbeat cycle.

The filtering function will generate some attenuation on the respiration signals, so the data received after filtering need a gain compensation. The attenuation coefficient may be obtained in advance via simulation experiment, for example, the attenuation is about −2.79 dB when the heartbeat rate is 70 BPM and the respiratory rate is 30 BPM. An attenuation coefficient table may be pre-established, and the attenuation coefficient corresponding to a parameter condition may be obtained by looking up in this table, so that a corresponding gain compensation coefficient may be set to compensate the respiration signal.

Figure 2:
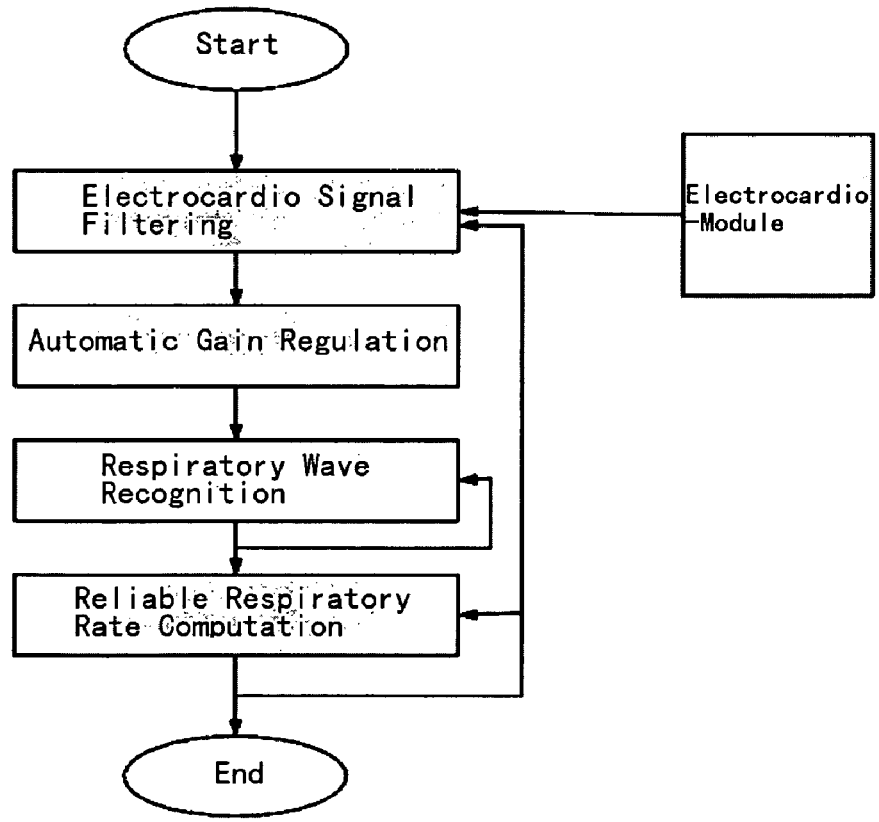
FIG. 2 is a flow chart of a complete processing of the method of the present invention.

In step C, when it is determined, via the above judgment, that the amplitude or frequency variation of the waveform is not beyond the predetermined range, it indicates that no strong heartbeat interference exists; in this case, as shown in FIG. 2, if a suitable software amplification is performed on the measured signal, then it will facilitate the recognition of said signal. Clinically, it is common that the respiration strength varies all the time; and generally, for a weak respiration, the gain of the signal needs to be regulated higher artificially. In order to avoid frequently changing the corresponding settings manually in the respiration measuring process, an automatic gain regulation function should necessarily be introduced clinically. This regulation differs from high-sensitivity recognition in that it will not separately amplify individual small interference signals within a group of large respiration signals, so that the interference signals will not be recognized as respiration signals.

Figure 7:
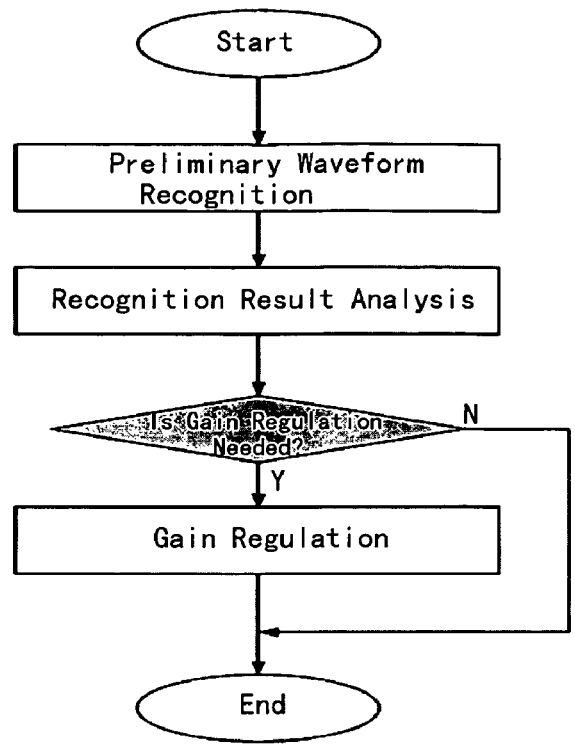
FIG. 7 is a flow chart of the automatic gain processing contained in the method of the present invention.

As shown in FIG. 7, the method of the present invention further comprises an automatic gain regulation process, in which it is judged whether the signal amplification coefficient should be increased or decreased according to a series of amplitudes and cycles obtained in a preliminary waveform recognition process. In said preliminary waveform recognition process, a small predetermined number of stairs may be set to recognize the crests and troughs, so that almost all the small signals can be recognized. If the fluctuation of said amplitude is small and said cycle meets predetermined requirements in a predetermined time period, then it indicates that the respiration signal is weak and the amplification coefficient of the received data may be increased in step A; otherwise, if the variations of the amplitude and cycle of waveform are not within the predetermined range in a predetermined time period, for example, if the signal is in an amplified state and a cut-off state occurs in a predetermined time period, then said amplification coefficient may be decreased. Said amplification of the received data may be realized via software in step A; besides, it may also be realized by controlling the lower machine via the upper machine. As a result, said data processing module will directly receive collected data amplified with a predetermined amplification coefficient. In the present invention, the automatic gain regulation may also facilitate the true or false judgment of the recognized respiratory crests and troughs via a self-adaptive threshold method (but it is not limited to be a necessary condition of the judgment).

Said self-adaptive threshold method differs from the prior art threshold method based on baselines in that it comprises three aspects: amplitude, time and area. According to the conditions of the true or false judgment, the threshold may be divided into absolute threshold and relative threshold: the former means that the current parameter must be within a predetermined numerical range; the latter means that the current parameter must be within a relative variation range, which refers to an optimum estimation of a characteristic parameter of a respiratory wave relative to the respiratory wave in a previous period of time. The self-adaptive method of the present invention is characterized in that the current reasonable respiratory wave will participate in the relative threshold computation of the next respiratory wave.

The conditions of the true or false judgment of a respiratory wave may be divided into necessary conditions and half sufficient conditions. Said necessary conditions may be set as: the amplitude must reach a predetermined threshold and the respiration cycle must be within a range (such as 0.4-6 seconds). Said half sufficient conditions mainly include two kinds of thresholds selected from the thresholds of amplitude, time and area. For example, for an adult, when the necessary conditions are met, if the cycle of a respiratory wave is within the range of 1.5 to 6 seconds (a half sufficient condition: absolute threshold), or the amplitude of a respiratory wave is above 60% of the average amplitude during 10 seconds before said respiratory wave (another half sufficient condition: relative threshold), then said respiratory wave may be regarded as a real respiratory wave.

Figure 8:
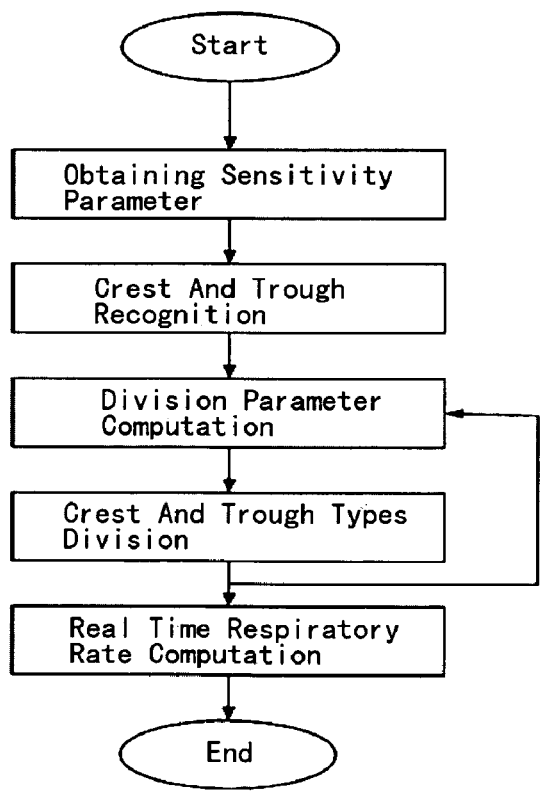
FIG. 8 is a flow chart of crest and trough self-adaptive threshold judgment contained in the method of the present invention.

As shown in FIG. 8, the process of the self-adaptive threshold crest and trough judgment according to the present invention comprises: obtaining a series of threshold parameters by sensitivity settings, wherein said parameters comprise the crest and trough recognition parameters (the count parameter, the predetermined number of stairs and the predetermined extent, etc.) of step B and the respiratory wave true or false judgment parameters of step C; then, the crests and troughs are recognized in step B; finally, in step C, the recognized respiratory crests or troughs are divided into various types via said threshold parameters, and the real crests and troughs are selected for realtime respiratory rate computation.

The following enumerated types may be employed to illustrate the divided types of the respiratory crests or troughs.

```
typedef enum
{
  PEAK = 5,               //real crest
  VALLEY = -5,            //real trough
  FAKE_PEAK = 3,          //a false crest
  FAKE_VALLEY = -3,       //a false trough
  PRE_PEAK_FAKE = 6,      //real crest, and the previous real
                          crest is forced to be set as a false crest
  PRE_VALLEY_FAKE = -6,   //real trough, and the previous real
                          trough is forced to be set as a false trough
  PEAK_FAKE_VALLEY = 4,   //real crest, and the previous false
                          trough is corrected as a real trough
  VALLEY_FAKE_PEAK = -4,  //real trough, and the previous
                          false
                          crest is corrected as a real crest
  NOTHING = 0             //neither a crest nor a trough
} PVTYPE;
```

Wherein, the conditions for being determined as a real crest (or a real trough) are that the necessary conditions and either of the half sufficient conditions must be met.

The conditions for being determined as a false crest (or a false trough) are that the necessary conditions are not met or either of the half sufficient conditions is not met.

The correction conditions for wrong recognitions are as follows: if a real crest (trough) is recognized first, and then another crest (trough) is recognized without a trough (crest) being recognized, and if said another crest (trough) is higher (lower) than the previous crest (trough), then said another crest (trough) will be set as a real crest (trough), while the previous crest (trough) will be set as a false crest (trough). This corresponds to a practical situation at which interferences usually exist, and in this case, two crests or troughs may be recognized sequentially from time to time, one of which usually is a small interference crest or interference trough.

The supplementary conditions for miss-recognitions are as follows: if a false crest (trough) is recognized first, it is assumed that this recognition is a result of the fact that time (half a respiration cycle) cannot meet the absolute conditions; at this time, another trough (crest) is recognized; if the sum of the time corresponding to said another trough (crest) and the previous false crest (trough) is equivalent to the current respiration cycle, then a serious baseline drift may be regarded as the cause of a miss-recognition, thus, the previous false crest (trough) may be recognized complementarily as a real crest (trough).

As a result, the recognition rate of a respiratory wave and the correctness of the recognition may be effectively improved by the division of crest and trough types.

Figure 9:
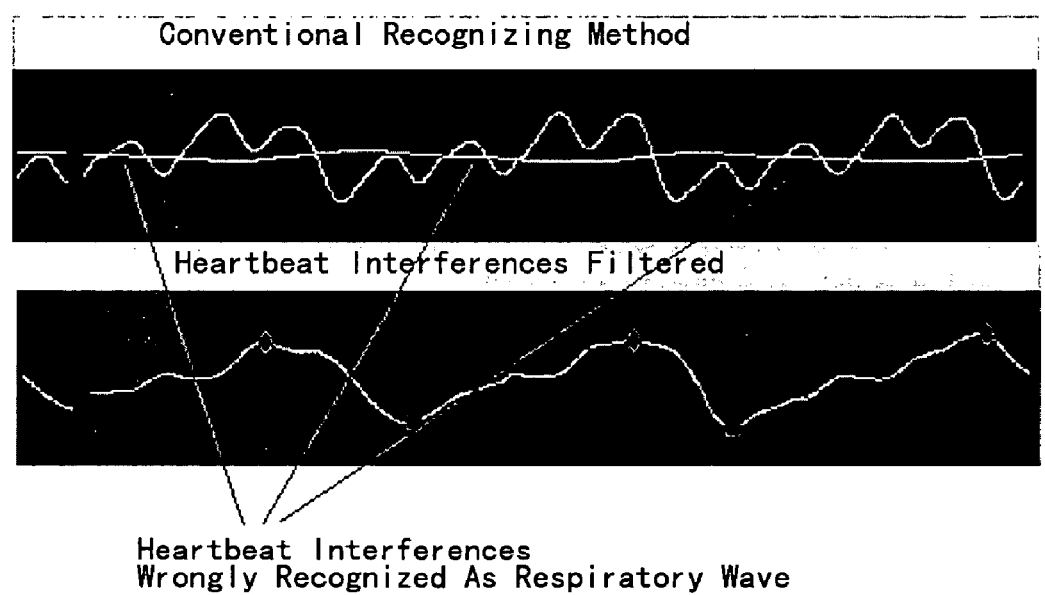
FIG. 9 is a comparison diagram of the crest and trough recognition under CVA between the method of the prior art and the method of the present invention.

It has been proved by experiments that when the respiration signal is ideal, the result obtained by the novel recognizing method of FIG. 2 according to the present invention and the result obtained by the conventional recognizing method are substantially consistent with each other; and when interferences exist, as shown in the test comparison (with CVA) of FIG. 9, the method of the present invention can eliminate wrong recognitions caused by interferences to a maximum extent and have high recognition rate and stability, so that the computing result of the respiratory rate can be more reliable.

The invention claimed is:

1. A method for improving the recognition of a respiratory wave, which is used for a data processing module of a respiratory rate measuring or monitoring device, said method comprising the steps of:
   A. receiving, via a data processing module, analog-to-digital converted respiratory wave data from a measuring circuit;
   B. sequentially searching, via the data processing module, the respiratory wave data for data corresponding to crests and troughs, each crest and trough comprising rising stairs and falling stairs; and
   C. identifying the crests and troughs of the respiratory wave data, wherein identifying the crests and troughs comprises determining that an amplitude or frequency variation of the waveform extends beyond a predetermined range and, based on the determination, filtering components of the waveform associated with a heartbeat through heartbeat filtering processing using a finite impulse response filter defined by $$y(n) = \frac{1}{L}\sum_{k=0}^{L-1}(n-k),$$

where x(n) is the measured respiratory wave data, y(n) is the result obtained after the heartbeat filtering of said data, and L is approximately the number of sampling points of the respiration in a heartbeat cycle.

2. The method for improving the recognition of a respiratory wave according to claim 1, wherein a searching process of said step of B comprises the steps of:
   a. comparing said respiratory wave data with data received before so as to determine whether the corresponding waveform is rising or falling;

b. recording the positions of the maximum or minimum values of the rising or falling in the searched data, when said rising or falling reaches its predetermined extent;

c. judging whether the overall tendency of the current data in the waveform is falling or rising so as to determine whether to recognize retroactively the recorded external position as the previous crest or trough; and d. taking the next respiratory wave data and returning to the step of a until the searching process of said step of B completes.

3. The method for improving the recognition of a respiratory wave according to claim 2, wherein count parameters are provided in said step of B for judging the rising or falling tendency of the waveform, said count parameters including a rising count, a maximum rising count, a falling count and a maximum falling count;

said count parameters are first initialized to 0 in said step of B; and in the sub-step of a, when the current data is larger than the previous data, if said rising count is less than twice of said predetermined number of stairs, then said rising count is increased by 1; if said falling count is larger than 0, then said falling count is decreased by 1; and if said maximum rising count is less than said rising count, then it will be set as the value of said rising count; when the current data is less than the previous data, if said falling count is less than twice of said predetermined number of stairs, then said falling count is increased by 1; if said rising count is larger than 0, then said rising count is decreased by 1; and if said maximum falling count is less than said falling count, then it will be set as the value of said falling count; and in the sub-step of c, when the values of said rising count and falling count are both equal to said predetermined number of stairs, the recorded extremal position will be recognized as the previous crest when the value of said maximum rising count is twice of said predetermined number of stairs, and said maximum rising count will be set as 0; and the recorded extremal position will be recognized as the previous trough when the value of said maximum falling count is twice of said predetermined number of stairs, and said maximum falling count will be set as 0; and in the sub-step of b, if the current data is larger than the previous data, then said predetermined extent will be set as said rising count and maximum rising count being equal to twice of said predetermined number of stairs; if the current data is less than the previous data, then said predetermined extent will be set as said falling count and maximum falling count being equal to twice of said predetermined number of stairs.

4. The method for improving the recognition of a respiratory wave according to claim 1, wherein said step of A further comprises a gain compensation processing for performing a gain compensation on the data obtained after said heartbeat filtering processing.

5. The method for improving the recognition of a respiratory wave according to claim 4, wherein in said gain compensation processing, a corresponding gain compensation coefficient is obtained by looking up in a pre-established attenuation coefficient table.

6. The method for improving the recognition of a respiratory wave according to claim 1, wherein said step of C further comprises: judging whether an amplitude or cycle variation of waveform is within a predetermined amplification range according to the data corresponding to each of the currently searched crests and troughs; if the variations of the amplitude and cycle of waveform are within the predetermined amplification range in a predetermined time period, then an amplification coefficient of the received data will be increased in said step of A or before said step of A; and if the variations of the amplitude and cycle of waveform are not within the predetermined amplification range in a predetermined time period, then said amplification coefficient will be decreased.

7. The method for improving the recognition of a respiratory wave according to claim 6, wherein said step of C further comprises the steps of judging true or false of each of said crests and troughs by using a self-adaptive threshold method, comprising:

i. obtaining a series of threshold parameters by sensitivity settings, said threshold parameters including parameters for judging true or false of respiratory crests and troughs;

ii. dividing each of the respiratory crests or troughs recognized in said step of B into various types by using said threshold parameters; and iii. determining and selecting real crests and troughs.

8. The method for improving the recognition of a respiratory wave according to claim 7, wherein the true and false of said respiratory crest or trough types can be converted therebetween, which comprises: reverting the wrongly recognized real crest or real trough to the false crest or false trough; or reverting the originally recognized false crest or false trough to the real crest or real trough which is miss-recognized.

9. The method for improving the recognition of a respiratory wave according to claim 1, wherein said step of C further comprises the steps of judging true or false of each of said crests and troughs by using a self-adaptive threshold method, comprising:

i. obtaining a series of threshold parameters by sensitivity settings, said threshold parameters including parameters for judging true or false of respiratory crests and troughs;

ii. dividing each of the respiratory crests or troughs recognized in said step of B into various types by using said threshold parameters; and iii. determining and selecting real crests and troughs.

10. The method for improving the recognition of a respiratory wave according to claim 9, wherein the true and false of said respiratory crest or trough types can be converted therebetween, which comprises: reverting the wrongly recognized real crest or real trough to the false crest or false trough; or reverting the originally recognized false crest or false trough to the real crest or real trough which is miss-recognized.

11. The method for improving the recognition of a respiratory wave according to claim 9, wherein the types of said respiratory crests or troughs include real crest, real trough, false crest or false trough; wherein, for a real crest and a real trough, both necessary conditions and either of half sufficient conditions must be met; and for a false crest and a false trough, the necessary conditions cannot be met or any of the half sufficient conditions cannot be met.

12. The method for improving the recognition of a respiratory wave according to claim 11, wherein said necessary conditions include that the amplitude of said crest or trough must reach a predetermined threshold and the respiration cycle must be within a predetermined range; and said half sufficient conditions include two kinds of predetermined thresholds selected from the thresholds of amplitude, time and area.

13. The method for improving the recognition of a respiratory wave according to claim 11, wherein the true and false of said respiratory crest or trough types can be converted therebetween, which comprises: reverting the wrongly recognized real crest or real trough to the false crest or false trough; or reverting the originally recognized false crest or false trough to the real crest or real trough which is miss-recognized.

14. A method for improving the recognition of a respiratory wave, which is used for a data processing module of a respiratory rate measuring or monitoring device, said method comprising the steps of:
  A. receiving, via a data processing module, analog-to-digital converted respiratory wave data from a measuring circuit;
  B. sequentially searching, via the data processing module, the respiratory wave data for data corresponding to crests and troughs, each crest and trough comprising rising stairs and falling stairs, wherein sequentially searching comprises:
    a. comparing said respiratory wave data with data received before so as to determine whether the corresponding waveform is rising or falling;
    b. recording the positions of the maximum or minimum values of the rising or falling in the searched data, when said rising or falling reaches its predetermined extent;
    c. judging whether the overall tendency of the current data in the waveform is falling or rising so as to determine whether to recognize retroactively the recorded external position as the previous crest or trough; and
    d. taking the next respiratory wave data and returning to the step of a until the searching process of said step of B completes;
  wherein count parameters are provided for judging the rising or falling tendency of the waveform, said count parameters including a rising count, a maximum rising count, a falling count and a maximum falling count;
  wherein said count parameters are first initialized to 0; and in the sub-step of a, when the current data is larger than the previous data, if said rising count is less than twice of said predetermined number of stairs, then said rising count is increased by 1; if said falling count is larger than 0, then said falling count is decreased by 1; and if said maximum rising count is less than said rising count, then it will be set as the value of said rising count; when the current data is less than the previous data, if said falling count is less than twice of said predetermined number of stairs, then said falling count is increased by 1; if said rising count is larger than 0, then said rising count is decreased by 1; and if said maximum falling count is less than said falling count, then it will be set as the value of said falling count; and
  wherein, in the sub-step of c, when the values of said rising count and falling count are both equal to said predetermined number of stairs, the recorded extremal position will be recognized as the previous crest when the value of said maximum rising count is twice of said predetermined number of stairs, and said maximum rising count will be set as 0; and the recorded extremal position will be recognized as the previous trough when the value of said maximum falling count is twice of said predetermined number of stairs, and said maximum falling count will be set as 0; and
  wherein, in the sub-step of b, if the current data is larger than the previous data, then said predetermined extent will be set as said rising count and maximum rising count being equal to twice of said predetermined number of stairs; if the current data is less than the previous data, then said predetermined extent will be set as said falling count and maximum falling count being equal to twice of said predetermined number of stairs; and
  C. identifying the crests and troughs of the respiratory wave data, wherein identifying the crests and troughs comprises determining that an amplitude or frequency variation of the waveform extends beyond a predetermined range and, based on the determination, filtering components of the waveform associated with a heartbeat through heartbeat filtering processing using a finite impulse response filter.

* * * * *